United States Patent [19]
Lopes

[11] Patent Number: 5,942,478
[45] Date of Patent: Aug. 24, 1999

[54] MICROBICIDAL AND SANITIZING SOAP COMPOSITIONS

[76] Inventor: John A. Lopes, 2209 Niagara Dr., Troy, Mich. 48083

[21] Appl. No.: 08/923,616

[22] Filed: Sep. 4, 1997

Related U.S. Application Data

[63] Continuation of application No. 08/530,680, Sep. 19, 1995, abandoned.

[51] Int. Cl.$^6$ ....................................................... A61K 7/24
[52] U.S. Cl. ........................... 510/130; 510/131; 510/137; 510/124; 510/127; 510/129; 424/44; 424/49; 424/55; 424/56; 424/20.1; 424/20.24
[58] Field of Search ................................... 510/130, 13.1, 510/137, 119, 124, 127, 129; 424/70.1, 70.5, 70.11, 70.12, 70.13, 70.22, 70.24, 78.02, 55, 49, 56, 44

[56] References Cited

U.S. PATENT DOCUMENTS

| | | | |
|---|---|---|---|
| 3,962,417 | 6/1976 | Howell | 424/52 |
| 4,088,597 | 5/1978 | Morlock | 252/106 |
| 4,108,981 | 8/1978 | Muhler | 424/55 |
| 4,150,151 | 4/1979 | Pader | 424/56 |
| 4,213,961 | 7/1980 | Curtis | 424/54 |
| 4,256,731 | 3/1981 | Curtis | 424/54 |
| 4,477,438 | 10/1984 | Willcockson | 424/130 |
| 4,545,979 | 10/1985 | Ambice | 424/52 |
| 4,550,018 | 10/1985 | Ambice | 424/52 |
| 4,919,918 | 4/1990 | Cole | 424/44 |
| 4,925,655 | 5/1990 | Smidel | 424/52 |
| 4,945,110 | 7/1990 | Brokken | 514/517 |
| 4,961,923 | 10/1990 | Hyde | 424/49 |
| 4,971,785 | 11/1990 | Wilson | 424/44 |
| 4,980,152 | 12/1990 | Frazier | 424/52 |
| 5,043,357 | 8/1991 | Hoffler | 514/553 |
| 5,122,541 | 6/1992 | Eddensperger | 514/578 |
| 5,143,720 | 9/1992 | Lopes | 424/55 |
| 5,534,265 | 7/1996 | Fowler et al. | 424/489 |
| 5,607,980 | 3/1997 | McAtee et al. | 514/476 |

FOREIGN PATENT DOCUMENTS

| | | |
|---|---|---|
| 3229097 | 8/1993 | Germany . |
| 2216419 | 2/1994 | United Kingdom . |

*Primary Examiner*—Necholus Ogden
*Attorney, Agent, or Firm*—Young & Basile, P.C.

[57] ABSTRACT

This invention relates to microbicidal and sanitizing soap compositions. More particularly, the invention relates to microbicidal and sanitizing soap compositions that incorporate agents with tuberculocidal properties in ready-to-use form that has gel properties or thixotropic-properties and to soap concentrate compositions suitable for dilution in or with water or non-aqueous diluent to produce gel-like or thixotropic solutions or dispersions ranging from free flowing to solidified forms. The ready-to-use compositions and the concentrate compositions are applied for purposes of personal or animal hygiene or sanitizing on hair, hands and skin or other body parts, or are applied on inanimate surfaces and objects that need to be sanitized.

21 Claims, No Drawings

MICROBICIDAL AND SANITIZING SOAP COMPOSITIONS

This is a continuation of application Ser. No. 08/530,680 filed on Sep. 19, 1995 now abandoned.

TECHNICAL FIELD

This invention relates to microbicidal anionic surfactant soap compositions useful for personal hygiene and for cleansing and sanitizing surfaces of human skin and non-skin surfaces, and for thereby preventing the risk of infection by microorganisms. The soap compositions in low pH use form are unexpectedly free of irritating and drying effect on skin normally associated with skin care compositions having a high concentration of surfactants at low pH.

BACKGROUND OF THE INVENTION

Conventional soap compositions for skin care and for general use sanitizing commonly have an unpleasant odor or are high in cost or are toxic. Chlorine bases products are harmful to the environment; also certain chlorine based products are not available to the public except in health-care institutions. The present novel soap compositions of the invention are economical and are microbicidal for preventing surface or topical infection without the drawbacks of available sanitizing soap products.

Anionic surfactants are commonly used in cleaning compositions and are also used as sanitizers or disinfecting solutions. However, for use as soap the anionic surfactant must be present in sufficient amount to generate foam for cleaning purposes, such as washing hands and for general personal hygiene, facial conditioning, and the like. The use of high concentration anionic surfactants and other surfactant containing compositions can at low pH result in damage to the skin, dryness, cracking, chapping, and irritation of the skin. Thus, anionic surfactants at low pH have not been used as microbicidal and sanitizing soaps on skin and body surfaces.

Aqueous sanitizing and disinfecting compositions which contain an anionic surfactant and an acidic component generally have short shelf lives because most surfactants lack the requisite stability in aqueous acidic solution. It is therefore an object of the present invention to provide microbicidal and sanitizing soap compositions in either solid, powder, liquid or gel form which are suitable for human and animal hygiene, such as when used for disinfecting hair, hands and skin and for general sanitizing purposes.

SUMMARY OF THE INVENTION

The present invention provides microbicidal and sanitizing soap compositions either in ready-to-use form or in soap concentrate form that is dilutable with a liquid carrier such as water. The compositions have the following advantages especially in the soap concentrate form: a) shelf-stability while containing acid-unstable anionic surfactants; b) low cost formulation (only concentrated chemical components are used); c) cost savings in transporting and storing the finished formulations (the bulk of water can be excluded); d) elimination of the difficulties in preparing concentrated aqueous formulations with ingredients of low aqueous solubility; e) readily usable novel nonaqueous formulations for personal hygiene; and f) convenience in carrying personal sanitizers. Moreover, the concentrate formulations do not have the instability problems associated with concentrated aqueous formulations at low temperatures.

DETAILED DESCRIPTION

The invention in one preferred embodiment concerns a soap concentrate composition, capable in use of dilution with pH-adjustable topical diluent to form a microbicidal solution or dispersion for use in protecting skin and non-skin surfaces against infection. The soap composition consists essentially of:

a) an anionic surfactant present in said use form in an amount in the range from about 0.10 weight percent to about 95 weight percent based on the total weight of the concentrate composition, b) a skin-lubricating and skin-protecting agent selected from natural gum polymers and synthetic gum polymers of the group consisting essentially of polysaccharide based xanthan, arabic, ghatti, carrageenin, karaya, tragacanth, agar-agar, Irish moss, Iceland moss, algin, guar, locust kernel, locust bean, quince seed, pectins, dextrins, cellulose ethers, modified starch and cellulose polymers, acrylate polymers, carboxylate polymers, sulfated polymers, poloxamers, and silicone based polymers, and mixtures of two or more said polymers, the skin-lubricating agent and skin-protecting agent in said use form being present in an amount ranging from 0.1 weight percent to about 25 weight percent based on the total weight of the concentrate composition, and c) an acidifying agent selected from acids of the group consisting essentially of acetic acid, adipic acid, ascorbic acid, citric acid, dehydroacetic acid, erythorbic acid, fumaric acid, glutaric acid, gluconic acid, hyaluronic acid, glycolic acid, lactic acid, malic acid, sorbic acid, succinic acid, tannic acid, tartaric acid, sulfuric acid, phosphoric acid, nitric acid, hydrochloric acid, sulfamic acid, carboxylic acid polymers, homo- or hetero-polymerized α-hydroxy carboxylic acids including poly lactic acid and poly lactic-glycolic acid and mixtures of two or more said acids, said acidifying agent being present in the concentrate composition in an amount fixing the use form pH thereof below pH 5.

The invention in a preferred embodiment includes the above described microbicidal soap composition having the components a), b), and c) and also comprises d) a skin conditioner component selected from the group of conditioners consisting of aloe vera, vitamins A, C, D, and E, menthol, thymol, tea tree oil, natural plant extract, sea weed extract, protein hydrolysates, fatty alcohols, fatty alcohol esters, sphingolipids, and mixtures of 2 or more said conditioners, in an amount ranging from 0.01 weight percent to about 10 weight percent based on the total weight percent of the concentrate composition.

The invention in another preferred embodiment includes the above described microbicidal soap composition having the components a), b), c) and d) and also comprises e) a component generally regarded as safe (GRAS) selected from the group of components consisting of benzoic acid, benzoic acid salts, benzoic acid esters, sorbic acid, sorbic acid salts, sorbic acid esters, parabens, alkyl lactylate esters, citrate esters, alkyl malate esters, alkyl glycolate esters, fatty acids, fatty acid salts and fatty acid esters, and mixtures of two or more said components in an amount ranging from about 0.05 weight percent to about 15 weight percent based on the total weight percent of the concentrate composition.

The compositions may comprise optional components described below.

In another preferred embodiment, the concentrate compositions are in the form of a gel or thixotrope that when applied to body surfaces or sanitizable surfaces within minutes is also microbicidally effective. The acidic component of these compositions may function both to lower the pH upon dilution with water and as the liquid carrier for the other components.

In another embodiment, the compositions when ready to use have exceptional activity against gram positive and gram negative bacteria such as *E. coli,* Staph. Aureus, *Mycobacterium tuberculosis, candida albicans,* Ps. Aeruginosa and salmonella typhi. The term "mycobacterical" means that such compositions containing surfactant at pH<3 in diluted use form are cidal for *Mycobacterium tuberculosis* when applied to body surfaces or sanitizable surfaces within one-half to two minutes.

In another preferred embodiment the microbicidal and sanitizing soap compositions comprise:

a) an anionic surfactant,
b) a skin lubricating and skin-protecting agent selected from natural gum polymers and synthetic gum polymers, and
c) an acidifying agent, as described, and may optionally contain,
d) emollients and/or skin conditioning agents that do not affect germ killing properties,
e) chemical agents, classified by the U.S. FDA as generally recognized as safe (GRAS) with antimicrobial properties, and if in ready-to-use form, f) a diluent or carrier or dissolve and/to disperse the above ingredients, said diluent being selected from the group consisting of water, ethanol, propanols, glycols, and mixtures of two or more said diluents.

The compositions may be in a dry powdered form or, alternatively, in a liquid form in a carrier in which the active components of the mixture are miscible or dilutable. In certain embodiments the acidic component of the compositions serves a dual role as both acidic component and anhydrous carrier.

Depending on the intended end use, the compositions may further contain components such as flavoring agents, sweeteners, coloring agents, and inorganic or organic salts. For example, when used as oral rinses or mouthwashes, the microbicidal and sanitizing compositions of the invention optionally contain sweeteners, colorants, and flavoring agents in addition to the surfactant, lubricant, and acidifying agents. When used for disinfecting hands, skin or hair, the formulations as indicated may contain emollients or conditioning agents. In formulations containing a nonaqueous carrier, the carrier may also provide emollient and conditioning functions.

The anionic surfactant agent, lubricant, skin conditioner, acidic components, flavoring agents, colorants, sweeteners, and salts utilizable in the compositions are selected from the class of substances generally regarded as safe (GRAS) or which have been ascribed food additive status as those terms are defined by the United States FDA in the Code of Federal Regulations, Chapter 21, Parts 178, 182 and 184, or which have low toxicity and have been approved for specific uses by the regulatory agencies.

ANIONIC SURFACTANT

Preferably the anionic surfactant of the compositions includes the free acid or salt forms (e.g., the ammonium, sodium, potassium calcium and magnesium salts) of (a) $C_6$–$C_{18}$ alkyl- and alkenylsulfates;
(b) $C_6$–$C_{18}$ alkyl- and alkenyl ether sulfates;
(c) $C_8$–$C_{16}$ alkyl diphenyl ether disulfonates;
(d) $C_4$–$C_{18}$ fatty acid isethionates;
(e) $C_6$–$C_{18}$ alkyl- and alkenylsulfonates;
(f) dialkyl- and dialkenyl sulfosuccinates in which the alkyl or alkenyl groups independently contain from six to eighteen carbon atoms;
(g) alkylbenzenesulfonates in which the alkyl group contains from six to eighteen carbon atoms;
(h) naphthalenesulfonates;
(i) alkylnaphthalenesulfonates in which the alkyl group contains from one to six carbon atoms;
(j) the mono- (n-alkyl) and mono- (n-alkenyl) acyl esters of $C_2$–$C_4$ hydroxylated monocarboxylic acids, in which the alkyl or alkenyl group contains from six to eighteen carbon atoms;
(k) the mono- (n-alkyl) and mono- (n-alkenyl) acyl esters of $C_2$–$C_4$ hydroxylated dicarboxylic acids, in which the alkyl or alkenyl group contains from six to eighteen carbon atoms;
(l) the mono- (n-alkyl) and mono- (n-alkenyl) alkyl esters of $C_2$–$C_4$ dicarboxylic acids, in which the alkyl or alkenyl group contains from six to eighteen carbon atoms, and
(m) $C_4$–$C_{18}$ fatty alcohol sulfoacetates.

By the term "alkyl" as used throughout this specification and the appended claims is meant a monovalent straight or branched chain hydrocarbon radical which can be thought of as derived from a saturated acyclic hydrocarbon by the removal of one hydrogen atom. By the term "alkenyl" is meant a monovalent hydrocarbon radical containing one or more carbon-carbon double bonds, which radical can be thought of as being derived from an unsaturated acyclic hydrocarbon by the removal of one hydrogen atom.

The term, "salt of a mono- (n-alkyl) or mono- (n-alkenyl) acyl ester of $C_2$–$C_4$ hydroxylated monocarboxylic acids" means an ester-salt of a hydroxylated monocarboxylic acid, such as lactic acid, which has been formed by esterification of its hydroxyl function by another acid, and in which its carboxyl function has been converted to a carboxylate salt. An example of such a compound is so-called "decyl lactylate" which is the ester formed by esterifying the hydroxyl group of lactic acid with decanoic acid, and converting the carboxyl function of the lactic acid portion of the resulting ester to the carboxylate salt form.

Similarly, the term, "salt of a mono- (n-alkyl) or mono- (n-alkenyl) acyl ester of $C_2$–$C_4$ hydroxylated dicarboxylic acids" means an ester-salt or a hydroxylated dicarboxylic acids, such as hydroxymalonic acid, such as hydroxymalonic acid, which has been formed by esterification of its hydroxyl function by another acid, and in which its two carboxyl functions have been converted to carboxylate salts.

By the term "salt of a mono- (n-alkyl) or mono- (n-alkenyl) alkyl ester of $C_2$–$C_4$ dicarboxylic acids" is meant an ester-salt of dicarboxylic acid, such as succinic acid, which has been formed by esterification by an alcohol at one carboxyl group.

Preferred anionic surfactants for the compositions include free acids or the ammonium, sodium, potassium, calcium or magnesium salts of 1) alfa olefin ($C_{14}$–$C_{16}$) sulfonic acid; 2) $C_4$–$C_{18}$ fatty acid isethionic acid; 3) $C_4$–$C_{18}$ fatty alcohol sulfoacetic acid; 4) decyl lactylic acid; 5) lauryl sulfuric acid; and 6) 1, 4 -dihexyl sulfosuccinic acid.

SKIN-LUBRICATING AND SKIN-PROTECTING AGENT

The skin-lubricating and skin-protecting agent of the compositions include natural gum polymers and synthetic gum polymers as described above. The skin-lubricating agent and skin-protecting agent in ready-to-use form has gel properties and/or thixotropic properties. In a soap concentrate composition form, capable of dilution to form a solution or dispersion that is ready to use, the polymer content is preferably present in an amount ranging from 0.1 weight percent to about 25 weight percent based on the total weight of the concentrate composition.

Preferred anhydrous solvents or carriers for the compositions are selected from propanol, isopropanol, propylene glycol, acetic acid, hydroxyacetic acid, propionic acid and mixtures thereof.

SWEETENING AGENTS

Suitable sweetening agents for use in the compositions include aspartame, acesulfame potassium, dextrose, invert sugar, saccharin, sorbitol, and sucrose. Flavoring agents include those well known to practitioners of the pharmaceutical and formulation arts including artificial and/or natural strawberry, cherry, raspberry, lemon and lime flavorants as well as menthol and ethyl alcohol.

SEQUESTERING AGENTS

Components may also be included in the solid dry formulations to act as sequestering agents or to reduce the cloudiness which might otherwise result when the compositions are dissolved in hard water. Components which may be employed for these purposes include organic compounds such as ethylene diamine tetraacetic acid (EDTA), organic salts and inorganic salts such as acid phosphates and acid pyrophosphates, and the chlorides, sulfates, citrates, nitrates, acetates, and lactates of potassium sodium, ammonium, and zinc. For example, sodium sulfate is used in amounts ranging between about 5 and 85 weight percent and zinc sulfate or sodium citrate are used in amounts of about 5 to about 50 weight percent in the dry solid compositions. While not adhering to any theory to the exclusion of others, it is believed that sodium sulfate, zinc sulfate, and sodium citrate control cloudiness by controlling the critical micelle concentration of the resulting aqueous solutions. Similarly, sodium acid phosphate is used in the dry solid compositions in concentrations ranging between about 5 to 85 weight percent. The sodium acid phosphate is believed to act both as a sequestering agent and as an agent to control critical micelle concentration.

The microbicidal and sanitizing compositions may be successfully employed in sanitizing and disinfecting food handling equipment and machinery such as found in clinics, hospitals, kitchens, dairies, breweries, food packing and canning facilities, beverage plans and the like. Moreover, the compositions can be used to prepare aqueous microbicidal solutions for the direct sanitizing of foods such as fresh fruits and vegetables. In this embodiment, the acidic component of the formulations may contain compounds such as citric acid, ascorbic acid or erythorbic acid which retard the browning of fresh fruits and vegetables.

When enhanced with flavoring and sweetening agents, the concentrate compositions can be used to prepare aqueous disinfecting solutions for use as mouth washes and oral rinses. When combined with emollients, conditioner agents, perfumes and coloring agents, the compositions can be diluted either with water or with a suitable non-aqueous diluent for use as microbicidal or sanitizing preparations for the hair, hands, and skin.

DRY POWDERED CONCENTRATE COMPOSITIONS

Dry, powdered concentrate compositions suitable for use in sanitizing and disinfecting food handling and processing equipment (as well as in other applications where compatibility with food for human and animal consumption is a prerequisite) comprise from between about 0.1 weight percent to about 95 weight percent anionic surfactant, from 0.1 weight percent to about 25 weight percent skin-lubricating and- protecting polymeric gel with the balance comprising an acidic component in salt or free acid form based on the total weight of the concentrate composition as described above.

ANHYDROUS LIQUID CONCENTRATE SANITIZER

Anhydrous liquid concentrate sanitizer formulations in a preferred embodiment comprise from between about 0.1 weight percent to about 95 weight percent anionic surfactant component, acidifying agent to adjust the pH to below pH 5, and the balance comprising an anhydrous solvent, preferably propylene glycol, based on the total weight of the concentrate composition. The propylene glycol may be replaced by the acidic component, as in the case of glacial acetic acid, or propionic acid. Small amounts, ranging from 0.1 weight percent to about 3 weight percent of a fatty acid of from eight to twelve carbon atoms may also be added to the mixture.

Dry, solid formulations particularly suited for dilution just prior to use as an oral rinse or mouthwash comprise from about 0.1 weight percent to about 7.5 weight percent of an anionic surfactant, and acid acidifying agent to adjust the pH of the solution to below pH 5.

Dry, solid formulations also particularly suited for dilution just prior to use as an oral rinse or mouthwash comprise from about 0.025 weight percent to about 5 weight percent anionic surfactant, from about 2 weight percent to about 35 weight percent citric acid, from about 7 weight percent to about 15 weight percent flavoring agent, and from about 1 weight percent to about 90 weight percent sweetener.

Depending on the intended end use the concentrate formulations of the invention are diluted with either water or a suitable non-aqueous diluent such as propylene glycol based on the total weight of the concentrate composition. Aqueous microbicidal solutions are prepared, for example, by diluting from 0.01 parts by weight percent to about 15 parts by weight percent of the concentrate with sufficient water to make 100 parts of aqueous solution. For use as an oral rinse or mouthwash, between about 0.5 parts by weight percent to 25 parts by weight percent of the concentrate mixture are diluted with sufficient water to make 100 parts by weight. In a preferred embodiment, the concentrate may comprise sodium fluoride, preferably at about 0.005 to about 2 weight percent, and/or dehydroacetic acid or its salt at about 0.005 to about 5 weight percent. For use as a microbicidal solution for sanitizing the surface of fresh fruits and vegetables, between about 0.01 and about 10 parts by weight percent of the concentrates of the present invention are diluted with sufficient water to make 100 parts by weight of solution. For use as waterless microbicidal preparations for the hair, hands and skin, between about 0.01 weight percent and about 20 weight percent of the concentrates are diluted with sufficient non-aqueous diluent to make 100 parts by weight total. The concentrates can be diluted or mixed with suitable inert ingredients, fillers, and binders, and molded into bar form for use as sanitizing bar soaps. An excess amount of anionic surfactant may be used as a diluent.

When the microbicidal and sanitizing compositions are diluted with water or suitable non-aqueous solvents to form the solutions which are used in the various applications described herein, it is preferred that the concentration of the anionic surfactant component in the diluted solution falls within the range of about 5 to about 75,000 parts per million.

Within this range of anionic surfactant concentration, the compositions produce solutions in water or suitable non-aqueous solvents having excellent microbicidal and sanitizing activity against gram negative and gram positive bacteria as evidenced by the data presented below. In addition, the concentrated compositions exhibit exceptional chemical stability and shelf life and are convenient to store and transport because of their small volume.

In tests of the stability of the compositions, for example, no deterioration of the compositions or loss of microbicidal and sanitizing activity upon dilution with water was observed even after allowing the concentrate mixtures to stand for periods of up to six months.

The compositions are suitable for personal care, e.g., as skin care products and personal hygiene products such as soap, shampoos, toothpaste, mouthwash, creams, lotions, and the like. Also, the compositions may be applied to the skin for prolonged skin contact without causing irritation. These products can be prepared more economically since they do not require the usual preservative or they use a lesser amount of the preservative. The concentrate composition in a preferred embodiment comprises: a) an anionic surfactant selected from fatty acid isethionate salts and fatty alcohol sulfoacetate salts and being present in an amount of from about 0.1 weight percent to about 95 weight percent, based on the total weight of the concentrate composition; b) a skin-lubricating and skin-protecting polymeric gel and c) an acidifying agent, present in an amount effective to produce a pH of below pH 5.0 upon dilution with water to make an aqueous solution or dispersion in which a solution of the anionic surfactant is present in about 10 to about 100,00 parts per million.

Preferably, the anionic surfactant is selected from the group consisting of salts of fatty acid isethionates of formula

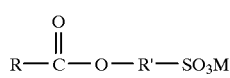

and fatty alcohol sulfoacetates of formula

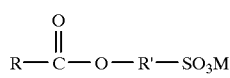

where R is an alkyl or alkenyl group with a chain length of 6 to 16 carbon atoms and R' is an alkyl or alkenyl group with a chain length of up to 4 carbon atoms, and M is a cationic group that forms a salt linkage with a sulfonic acid group, such as the ammonium, sodium, potassium, calcium and magnesium salts.

Preferably, the acidifying agent is selected from the group of acids consisting of acetic, adipic, ascorbic, citric, dehydroacetic, erythorbic acid, fumaric acid, glutaric acid, gluconic, hyaluronic, glycolic, lactic, malic, succinic, sulfamic, tannic, tartaric, and mixtures of two or more of these acids.

Microbicidal activity, as the term is used herein, is the lethal antimicrobial activity resulting in reduction of the microbial population by a magnitude of five logarithmic units within 30 to 60 seconds.

The preferred sulfonated esters are sodium salts of esters derived from sulfoacetic acid and isethionic acid. Sodium sulfoacetic acid esters are reaction products of a fatty alcohol and sulfoacetic acid. The fatty alcohol of choice has a carbon chain length of 6 to 16. The preferred fatty alcohol ester is a lauryl alcohol ester. A commercially available sodium salt of the ester of sulfoacetic acid, marketed by Stephan Co. under the trade name Lathanol LAL, is especially useful. Sodium isethionic acid esters are reaction products of fatty acids and isethionic acid. The fatty acids of choice are derived from coconut oil with predominant lauric acid (C12), myristic acid (C14), palmitic acid (C16), and oleic acid (C18). The sodium salt of the ester of isethionic acid is commercially available from Rhone Poulenc, American Hoechst Corporation and Mazer Chemicals Inc. A preferred salt is the sodium salt of the ester of isethionic acid marketed by Rhone Polene under the trade name Igepon AC-78.

The acidifying agent of the compositions for obtaining the desired microbicidal property must be compatible with the anionic surfactants. Preferred agents are acetic acid, adipic acid, ascorbic acid, citric acid, dehydroacetic acid, erythorbic acid, fumaric acid, glutaric acid, gluconic acid, gluconolactone, hyaluronic acid, hydroxyacetic acid, lactic acid, malic acid, polymerized carboxylic acids comprising polylactic and polylactic-glycolic acid, succinic acid, sulfamic acid, tannic acid, tartaric acid, and mixtures thereof.

The invention and the best mode of practicing the same are illustrated by the following examples of preferred embodiments thereof.

Example 1. Soap Composition

| Ingredient | Percentage | Grams (W/W) |
| --- | --- | --- |
| Sodium Alpha Olefin ($C_{14}$—$C_{16}$) Sulfonate (40%) | 10.0 | 100.00 |
| Lactic acid (88%) | 1.0 | 10.00 |
| Xanthan gum | 0.5 | 5.00 |
| Lemon flavor | 0.1 | 1.00 |
| Water | To 100 ml | To 1 liter |

Example 2. Soap Composition

| Ingredient | Percentage | Grams (W/W) |
| --- | --- | --- |
| Sodium Alpha Olefin ($C_{14}$—$C_{16}$) Sulfonate (40%) | 11.25 | 100.00 |
| Lactic acid (88%) | 1.0 | 10.00 |
| Xanthan gum | 0.5 | 5.00 |
| Aloe vera powder | 0.1 | 1.00 |
| Lemon flavor | 0.1 | 1.00 |
| Water | To 100 ml | To 1 liter |

Example 3. Soap Composition

| Ingredient | Percentage | Grams (W/W) |
| --- | --- | --- |
| Sodium Alpha Olefin ($C_{14}$—$C_{16}$) Sulfonate (90%) | 5.0 | 50.00 |
| Lactic acid (88%) | 1.0 | 10.00 |
| Xanthan gum | 0.75 | 7.50 |
| Lemon flavor | 0.1 | 1.00 |

All the above ingredients are mixed and stored. Hand soap is then reconstituted by dissolving in one liter of water prior to use.

Example 4. Soap Composition - Powder

| Ingredient | Percentage | Grams (W/W) |
|---|---|---|
| Sodium Alpha Olefin ($C_{14}$—$C_{16}$) Sulfonate (90%) | 50.0 | 50.00 |
| Lactic acid (88%) | 1.0 | 10.00 |
| Xanthan gum | 0.5 | 5.00 |
| Aloe vera powder | 0.2 | 2.00 |
| Lemon flavor | 0.1 | 1.00 |
| FD&C Green 3 | 0.0009 | 0.009 |

All the above ingredients are mixed and stored. Prior to use soap is reconstituted by dissolving the powder in water and making up the volume to one liter.

Example 5. Soap Composition - Liquid

| Ingredient | Percentage | Grams (W/W) |
|---|---|---|
| Sodium Alpha Olefin ($C_{14}$—$C_{16}$) Sulfonate (40%) | 10.93 | 163.95 |
| Lactic acid (88%) | 1.00 | 15.00 |
| Sodium chloride | 1.00 | 15.00 |
| Xanthan gum | 0.68 | 10.20 |
| Decyl lactylate | 0.50 | 7.50 |
| Aloe vera powder | 0.20 | 3.00 |
| Benzoic acid | 0.20 | 3.00 |
| FD & C Green #3 | 0.0008 | 0.012 |
| Water To | 100 ml | 1500 ml |

The antimicrobial properties of the sanitizing preparations were evaluated.

The test liquid composition of Example I was evaluated by the US FDA recommended method for oral disinfectants. The liquid product of Example 5 was evaluated by the USDA recommended method for hand washing and/or sanitizing compounds.

A method recommended by the US FDA for evaluating antiseptic oral health products offers a practical procedure for determining microbicidal properties of soap for use on skin surfaces. Both hand soap and mouthwash with antiseptic or disinfectant properties are designed for eliminating microorganisms from skin or mucosal surfaces after a very short contact period. The test procedure is described in the Federal Register, V.47, No. 101, p. 22898, Jan. 6, 1978.

The test method organisms used were Staph. Aureus ATCC 6538, *E. coli* ATCC 11229, Ps. Aeruginosa ATCC 10145, and *Candida albicans* ATCC 18804. These organisms represent gram positive and negative bacteria as well as yeast. The cultures were maintained either on nutrient agar or Sabouraud's agar for bacteria and yeast respectively. Prior to use, the cultures were transferred in broth medium for three consecutive days at 37° C. A 24-hour broth culture was used in the test. All the tests were carried out at 37° C. using a waterbath.

A 0.5 ml of the test culture was added to five ml of the test sample in a 25×125 ml medication tube and mixed with a vortex mixer. A loopful of the mixture was removed with a 10 μl sterile plastic loop and mixed with 10 ml of growth medium at intervals: 30 seconds, 1, 2, 3, 4 and 5 minutes. The growth medium (nutrient broth or Sabouraud's broth) contained 0.07% lecithin (United States Biochemical Corp., Cleveland, Ohio) and 0.55% Tween 80 (United States Biochemical Corp., Cleveland, Ohio) as neutralizing agents. Culture control consisted of 5 ml of sterile water in place of a test sample. The ability of growth medium to neutralize carry-over of the microbicidal agent, during transfer of the test mixture, was tested by first mixing a loopful, 10 μl, of the hand soap sample with the growth medium followed by a loopful of 1:10 dilution of the test inoculum. This served as neutralizer control.

The inoculated tubes were incubated at 37° C. The results were recorded after 48 hrs incubation by observing growth (turbidity) in the tubes. Tests were repeated with bacterial cultures using 30 and 60 seconds contact time. Yeast cultures were tested at a cell density of $1.21 \times 10^5$ CFU/ml.

The results of the microbiological tests are presented in Tables 3 to 7. Tables 3–5 show the activity of undiluted, 1:4 and 1:8 dilutions of hand soap against *S. aureus, E. coli,* and *Ps. aeruginosa*. Undiluted as well as diluted hand soap exhibit lethal activities against the test organisms in 30 seconds. Dilutions of the hand soap were selected to represent dilutions which normally occur during hand washing.

Table 6 presents the results of the tests repeated for 30 and 60 seconds of contact time with bacterial concentration of $0.98 \times 10^7$, $1.04 \times 10^7$, and $1.42 \times 10^7$ per ml for *S. aureus, E. coli,* and Ps. Aeruginosa, respectively. Since 0.5 ml of the culture is added to 5 ml of the test sample, the resulting bacterial number is reduced approximately by one logarithmic unit. Absence of growth in the growth medium inoculated with a loopful of the test mixture can be assumed to contain less than one surviving cell out of $1.6 \times 10^5$, $1.39 \times 10^5$, and $4.55 \times 10^5$ cells, respectively in Tables 3, 4 and 5 and $0.98 \times 10^5$, $1.04 \times 10^5$, and $1.42 \times 10^5$ cells, respectively in Table 6 in 10 μl (1:100 dilution) corresponding to *S. aureus, E. coli,* and Ps. Aeruginosa. Thus the hand soap dilutions tested reduced bacterial population by 99.999% after 30 seconds of contact time. Table 5 shows that even further dilution of hand soap to 1:16 maintained microbicidal activity of the hand soap.

Table 7 shows the efficacy of the hand soap against *Candida albicans*. Because of the dilution of the inoculum, the concentration of cells in the test was $1.21 \times 10^5$ CFU/ml. The number of cells transferred in one loopful (10 μl) from the test mixture and inoculated in the growth medium was $1.21 \times 10^3$. Assuming the absence of growth in the growth medium is due to the absence of a single surviving cell in a loopful ($1.21 \times 10^3$ cells), the test sample killed 99.9% of yeast cells within one minute as seen in Table 6.

TABLE 3

Efficacy of Example 1 Soap Against *Staph. aureus*

(Challenge Number $1.61 \times 10^7$/ml)

| | Growth After Contact Time (seconds/minutes) | | | | | |
|---|---|---|---|---|---|---|
| Test Product | 30" | 60" | 2' | 3' | 4' | 5' |
| (undiluted) | – | – | – | – | – | – |
| (1:4) | – | – | – | – | – | – |
| (1:8) | – | – | – | – | – | – |
| Neutralizer control | +++ | | | | | |
| Control (water) | ++++ | | | | | |

– = No growth; + = Growth.

TABLE 4

Efficacy of Example 1 Soap Against *E. coli*

(Challenge Number $1.39 \times 10^7$/ml)

| Test Product | Growth After Contact Time (seconds/minutes) | | | | | |
|---|---|---|---|---|---|---|
| | 30" | 60" | 2' | 3' | 4' | 5' |
| (undiluted) | − | − | − | − | − | − |
| (1:4) | − | − | − | − | − | − |
| (1:8) | − | − | − | − | − | − |
| Neutralizer control | +++ | | | | | |
| Control (water) | +++ | | | | | |

− = No growth; + = Growth.

TABLE 5

Efficacy of Example 1 Soap Against *Ps. aeruginosa*

(Challenge Number $4.55 \times 10^7$/ml)

| Test Product | Growth After Contact Time (seconds/minutes) | | | | | |
|---|---|---|---|---|---|---|
| | 30" | 60" | 2' | 3' | 4' | 5' |
| (undiluted) | − | − | − | − | − | − |
| (1:4) | − | − | − | − | − | − |
| (1:8) | − | − | − | − | − | − |
| Neutralizer control | +++ | | | | | |
| Control (water) | +++ | | | | | |

− = No growth; + = Growth.

TABLE 6

Bactericidal Activity of Example 1 Hand Soap against *S. aureus, E. coli,* and *Ps. aeruginosa*

| | Growth After Contact Time (seconds/minutes) | | | | | |
|---|---|---|---|---|---|---|
| | S. aureus ($0.98 \times 10^7$/ml) | | E. coli ($1.0 \times 10^7$/ml) | | Ps. aeruginosa ($1.42 \times 10^7$/ml) | |
| Test Product | 30" | 60" | 30" | 60" | 30" | 60" |
| (1:4 dilution) | − | − | − | − | − | − |
| (1:8 dilution) | − | − | − | − | − | − |
| (1:16 dilution) | − | − | − | − | − | − |
| Neutralizer control | +++ | | | | | |
| Control (water) | +++ | NA | ++ | NA | ++ | NA |

− = No growth: + = Growth.

TABLE 7

Efficacy of Soap Example 1 Against *Candida albicans*

(Challenge Number $1.21 \times 10^5$/ml)

| Test Product | Growth After Contact Time (seconds/minutes) | | | | | |
|---|---|---|---|---|---|---|
| | 30" | 60" | 2' | 3' | 4' | 5' |
| (undiluted) | + | − | − | − | − | − |
| (1:4 dilution) | + | − | − | − | − | − |
| (1:8 dilution) | + | − | − | − | − | − |
| Neutralizer control | +++ | | | | | |
| Control (water) | +++ | | | | | |

− = No growth; + = Growth.

Evaluation of the microbicidal soap composition by the Available Chlorine Germicidal Equivalent Concentration Test The sanitizing properties of the soap were evaluated by the Available Chlorine Germicidal Equivalent Concentration test method. The method is recommended by the USDA for evaluating hand washing and/or sanitizing compounds.

The test organisms used were *S. aureus* ATCC 6538 and *Salmonella typhi* ATCC 6539.

The results in Table 8 and 9 show that the soap composition even when diluted with water retained both sanitizing and microbicidal activities. It showed lethal activity equivalent to 200 ppm of hypochlorite against *S. aureus* at a dilution of the 1:128 and against *Salmonella typhi* at dilution of 1:48. Since the sanitizing and microbicidal soap composition is to be used in undiluted form, the invention offers a powerful germ killing soap composition even after dilution with water such as may occur during washing.

TABLE 8

AOAC Available Chlorine Germicidal Equivalent Test against *S. aureus* ATCC 6538

| Test Sample | Conc.: ppm of AvC12/ Dilution | Growth in Subculture Tube Number | | | | | | | | | |
|---|---|---|---|---|---|---|---|---|---|---|---|
| | | 1 | 2 | 3 | 4 | 5 | 6 | 7 | 8 | 9 | 10 | * |
| NaOCl | 200 | − | − | − | − | − | − | + | + | + | + | + |
| | 100 | − | − | − | + | + | + | + | + | + | + | + |
| | 50 | − | − | + | + | + | + | + | + | + | + | + |
| Soap (Example 5) | Undil. | − | − | − | − | − | − | − | − | − | − | + |
| | 1:16 | − | − | − | − | − | − | − | − | − | − | + |
| | 1:32 | − | − | − | − | − | − | − | − | − | − | + |
| | 1:64 | − | − | − | − | − | − | − | − | − | − | + |
| | 1:128 | − | − | − | − | − | − | + | + | + | + | + |
| | 1:256 | − | − | + | + | + | + | + | + | + | + | + |
| | 1:512 | + | + | + | + | + | + | + | + | + | + | + |

+ = growth in subculture; − = no growth in subculture
* = Neutralizing growth medium control

TABLE 9

AOAC Available Chlorine Germicidal Equivalent Test against *Salmonella typhi* ATCC 6539

| Test Sample | Conc.: ppm of AvC12/ Dilution | Growth in Subculture Tube Number | | | | | | | | | |
|---|---|---|---|---|---|---|---|---|---|---|---|
| | | 1 | 2 | 3 | 4 | 5 | 6 | 7 | 8 | 9 | 10 | * |
| NaOCl | 200 | − | − | − | − | − | − | + | + | + | + | + |
| | 100 | − | − | − | − | + | + | + | + | + | + | + |
| | 50 | − | − | − | + | + | + | + | + | + | + | + |
| Soap (Example 5) | Undil. | − | − | − | − | − | − | − | − | − | − | + |
| | 1:16 | − | − | − | − | − | − | − | − | − | − | + |
| | 1:32 | − | − | − | − | − | − | − | + | + | + | + |
| | 1:48 | − | − | − | − | − | − | + | + | + | + | + |
| | 1:64 | − | − | − | − | + | + | + | + | + | + | + |
| | 1:128 | − | + | + | + | + | + | + | + | + | + | + |
| | 1:256 | + | + | + | + | + | + | + | + | + | + | + |

+ = growth in subculture; − = no growth in subculture
* = Neutralizing growth medium control Decyl lactylate was incorporated in the sanitizing and microbicidal soap composition to impart tuberculocidal activity. An aqueous solution of 300 ppm of decyl lactylate and 8800 ppm of lactic acid (pH <3.0) exhibited higher tuberculocidal activity than 100 ppm of hypochlorite when examined essentially by the AOAC germicidal and detergent sanitizer test. The tests carried out in 500 ppm of hard water solution consisted of lecithin with polysorbate 80 prepared in phosphate buffer pH 7.2. In case of hypochlorite 0.1 ml of 10% thiosulfate was added to each tube of the neutralizer solution.

The results are reported in Table 10.

TABLE 10

Lethal Activity: Decyl Lactylate Against *Mycobacterium tuberculosis*

CFU After Contact Time in Seconds/minutes

| Test Product | 30 Seconds | | 60 Seconds | | 5 Minutes | |
|---|---|---|---|---|---|---|
| | CFU | % Kill | CFU | % Kill | CFU | % Kill |
| Decyl lactylate | 179, 272 | >99.996 | 43, 19 | >99.999 | 6, 3 | >99.999 |
| | 312, 333 | >99.996 | 67, 72 | >99.999 | 13, 8 | >99.999 |
| NaOCl (100 ppm) | T, T | ND | T, T | ND | 82, 79 | >99.998 |
| | T, T | ND | T, T | ND | 110,147 | >99.997 |

Activity of decyl lactylate under acidic pH (<3.0)
CFU = colony forming unit, ND = Not determined, T = Too Numerous To Count (TNTC), Challenge Number of CFUs/ ml = 72 × 10$^6$ These results show that the composition containing decyl lactylate and lactic acid at pH 3.0 was tuberculocidal whereas NaOCl (100 ppm) was not.

Microbicidal properties of sodium isethionate (Igepon 78-C) and sodium sulfoacetate (Lathanol LAL) were examined in the formulated products. Microbicidal activities of the test compounds was evaluated by the germicidal and detergent sanitizer evaluation method recommended by the Association of Analytical Chemists (A.O.A.C.). It is essentially a suspension test method where a known concentration of the test compound in 99 ml solution is mixed with 1 ml of a standard suspension of microbial cells. The test was carried out at 25° C. An aliquot of the test mixture is transferred to neutralizing solution at 30 and 60 seconds respectively to stop the action of the test compound and the surviving number of cells are counted by plating on a nutrient medium incubated for 48 hours at 37 C. The test was carried out using *S. aureus* ATCC and *E. coli* ATCC 11229 representing gram positive and gram negative bacterial groups.

The test compounds were formulated with citric acid and sodium sulfate. COMPOSITION A consisted of 1.85% Igepon AC-78, 16.27% citric acid and 81.88% sodium sulfate. COMPOSITION B consisted of 2.35% Lathanol LAL, 16.19% citric acid and 81.46% sodium sulfate.

In the test either 1.95 g of COMPOSITION A containing Igepon AC-78 or 1.96 g of COMPOSITION B containing Lathanol LAL preparation per 100 ml of water were used resulting in 300 ppm of active compounds respectively, in the final test. The results are presented in the following Table 11.

TABLE 11

Microbicidal properties of disinfecting and sanitizing compositions of Igepon AC-78 and Lathanol LAL

| | | Staph. aureus | | E. coli | |
|---|---|---|---|---|---|
| | | Number of surviving cells after contact (seconds) | | | |
| | Conc. ppm | 30 | 60 | 30 | 60 |
| COMPOSITION A | | | | | |
| (IGEPON AC-78) | 300 | 190,176 | 8,5 | 25,25 | 0,0 |
| % KILL | | >99.998 | >99.999 | >99.999 | >99.999 |
| COMPOSITION B | | | | | |
| (LATHANOL LAL) | 300 | 28,36 | 0,0 | T,T | T,T |
| % KILL | | >99.999 | >99.999 | ND,ND | ND,ND |
| Hypochlorite | 50 | 0,0 | 0,0 | 0,0 | 0,0 |
| % KILL | | >99.999 | >99.999 | >99.999 | >99.999 |
| Untreated Control | | 110 × 10$^6$ | | 110 × 10$^6$ | |

T = Too numerous to count. 0 = No growth. ND = Not determined.

The examples presented above are merely illustrative and should not be read as limiting the scope of the invention as it is defined in the appended claims.

I claim:

1. A soap concentrate composition, capable for use in dilution with pH-adjustable topical diluent to form a microbicidal lubricating solution or dispersion for use in protecting skin and non-skin surfaces against infection, the soap composition consisting essentially of:
   a) an anionic surfactant present in said solution and/or dispersion form the range from about 0.1 weight percent to about 95 weight percent based on the total weight of the concentrate composition,
   b) a skin-lubricating and skin-protecting agent selected from natural gum polymers and synthetic gum polymers of the group consisting essentially of polysaccharide based xanthan, arabic, ghatti, carrageenin, karaya, tragacanth, agar-agar, Irish moss, Iceland moss, algin, guar, locust kernel, locust bean, quince seed, pectins, dextrins, cellulose ethers, starch and cellulose polymers, acrylate polymers, carboxylate polymers, sulfated polymers, polyvinyl pyrrolidones, poloxamers, and silicone based polymers, and mixtures of two or more said polymers, the skin-lubricating agent and skin-protecting agent in said use form being present in an amount ranging from 0.1 weight percent to about 25 weight percent based on the total weight of the concentrate composition, and
   c) an acidifying agent selected from acids of the group consisting essentially of acetic acid, adipic acid, ascorbic acid, citric acid, dehydroacetic acid, erythorbic acid, fumaric acid, glutaric acid, gluconic acid, hyaluronic acid, glycolic acid, lactic acid, malic acid, sorbic acid, succinic acid, tannic acid, tartaric acid, sulfuric acid, phosphoric acid, nitric acid, hydrochloric acid, sulfamic acid, carboxylic acid polymers, homo- or hetero- polymerized α-hydroxy carboxylic acids including poly lactic acid and poly lactic-glycolic acid and mixtures of two or more said acids, said acidifying agent being present in the concentrate composition in an amount adjusting the solution and/or dispersion form pH thereof below pH 5, said microbicidal protection resulting in reduction of the microbial population by a magnitude of five logarithmic units within 30 to 60 seconds.

2. A soap composition as in claim 1 comprising a skin conditioner component selected from the group of conditioners and moisturing agents consisting of aloe vera, vitamins A, C, D, and E, menthol, thymol, tea tree oil, plant extract, sea weed extract, protein hydrolysates, fatty alcohols, fatty alcohol esters, sphingolipids, and mixtures of 2 or more said conditioners, in an amount ranging from 0.01 weight percent to about 20 weight percent based on the total weight percent of the concentrate composition.

3. A microbicidal soap composition as in claim 1 comprising a generally regarded as safe GRAS compound selected from the group of components consisting of benzoic acid, benzoic acid salts, benzoic acid esters, sorbic acid, sorbic acid salts, sorbic acid esters, parabens, alkyl lactylate esters, citrate esters, alkyl malate esters, alkyl glycolate esters, fatty acids, fatty acid salts and fatty acid esters, and mixtures of two or more said components.

4. A soap concentrate composition as in claim 1 diluted in solution and/or dispersion form with diluent selected from the group of diluents consisting essentially of water, ethanol, propanols, glycols, and mixtures of two or more said diluents.

5. A soap concentrate composition as in claim 3 comprising a component of the group consisting of a free acid, salt or ester form of benzoic acid, dehydroacetic acid, mono- n-alkyl and mono- n-alkenyl acyl esters of C2–C4 hydroxylated monocarboxylic acids in which the alkyl or alkenyl group contains from six to eighteen carbon atoms, and mixtures of two or more said components, said component being present in an amount between 0.005% weight percent to about 20% weight percent based on the total weight of the concentrate composition.

6. A soap concentrate composition as in claim 5 wherein said components are sodium decyl lactylate, benzoic acid and dehydroacetic acid, and mixtures of two or more said components.

7. An acidifying agent as in claim 1 comprising a hydroxy acid selected from the group consisting of citric, glycolic, lactic, malic and tartaric acids, and mixtures of two or more said acids.

8. A soap composition as in claim 1 wherein the surfactant is selected from the group of surfactants consisting of the free acid or salt forms of:

C6–C18 alkyl- and alkenyl- sulfates;

C6–C18 alkyl- and alkenyl- ether sulfates;

C8–C16 alkyl diphenyl ether disulfonates;

C4–C18 fatty acid isethionates;

C6–C18 alkyl- and alkenyl sulfonates;

dialkyl- and dialkenyl sulfosuccinates in which the alkyl or alkenyl groups independently contain from six to eighteen carbon atoms;

C6–C18 alkylbenzene sulfonates;

naphthalene sulfonates;

alkyl naphthalene sulfonates in which alkyl group contains from one to six carbon atoms;

the mono- n-alkyl and mono- n-alkenyl acyl esters of C2–C4 hydroxylated monocarboxylic acids in which the Alkyl or alkenyl group contains from six to eighteen carbon atoms;

the mono- n-alkyl and mono- n-alkenyl acyl esters of C2–C4 hydroxylated dicarboxylic acids in which the alkyl or alkenyl group contains six to eighteen carbon atoms;

the mono- n-alkyl and mono- n-alkenyl alkyl esters of C2–C4 Dicarboxylic acids, in which the alkyl or alkenyl group contains from six to eighteen carbon atoms; and C4–C18 fatty alcohol sulfoacetates, and mixtures of two or more said surfactants.

9. A soap composition as in claim 8 comprising a surfactant of the group consisting of sodium alpha olefin $C_{14}$–$C_{16}$ sulfonate, sodium $C_4$–$C_{18}$ fatty acid esters of isethionate, sodium $C_4$–$C_{18}$ fatty alcohol esters of sulfoacetate, and mixtures of two or more said surfactants.

10. A soap concentrate composition as in claim 1 comprising a nonionic foaming agent selected from the group consisting of polyols, poloxamers, acyl derivatives of sugars, acyl derivatives of carbohydrates, and mixtures of two or more said nonionic foaming agents.

11. A microbicidal soap composition as in claim 1 wherein the skin-lubricating and skin-protecting agent serves as a thixotropic and/or solidifying agent.

12. A soap composition as in claim 1 in the form of a solid bar, dry powder, gel, liquid or a foaming product.

13. A microbicidal composition having tuberculocidal activity as in claim 8.

14. An antitubercular composition having antitubercular activity as in claim 8.

15. A composition as in claim 1 in solution and/or dispersion form comprising an anhydrous diluent for the composition selected from propanol, isopropanol, propylene glycol, acetic acid, hydroxyacetic acid, propionic acid, ethyl lactate, and mixtures thereof.

16. A composition as in claim 1 comprising a sequestering agent selected from ethylene diamine tetraacetic acid, sodium acid pyrophosphate, sodium phosphate, chlorides, sulfates, citrates, nitrates, acetates, and lactates of potassium, sodium, ammonium, and zinc, and mixtures of two more said sequestering agents.

17. A composition as in claim 16 wherein the concentrate composition is diluted with water in ready-to-use form.

18. A non-aqueous bactericidal and antimicrobial soap concentrate composition, capable for use in diluting with pH-adjustable topical diluent to form a bactericidal and antimicrobial lubricating solution or dispersion for use in protecting skin and non-skin surfaces against infection said solution or dispersion being cidal for *Mycobacterium tuberculosis* when applied to body surfaces or sanitizable surfaces within one-half to two minutes, the soap composition consisting essentially of:

a) an anionic surfactant present in said use form in an amount in the range from about 0.1 weight percent to about 95 percent based on the total weight of the concentrate composition, b) a skin-lubricating and skin-protecting agent selected from natural gum polymers and synthetic gum polymers of the group consisting essentially of polysaccharide based xanthan, arabic, ghatti, carrageenin, karays, tragacanth, agar-agar, Irish moss, Iceland moss, algin, guar, locust kernel, locust bean, quince seed, pectins, dextrins, cellulose ethers, modified starch and cellulose polymers, acrylate polymers, carboxylate polymers, sulfated polymers, polyvinyl pyrrolidones, poloxamers, and silicone based polymers, and mixtures of two or more said polymers, the skin-lubricating agent and skin-protecting agent in said use form being present in an amount ranging from 0.1 weight percent to about 25 weight percent based on the total weight of the concentrate composition, and c) an acidifying agent selected from acids of the group consisting essentially of acetic acid, adipic acid, ascorbic acid, citric acid, dehydroacetic acid, erythorbic acid, fumaric acid, glutaric acid, gluconic acid, hyaluronic acid, glycolic acid, lactic acid, malic acid, sorbic acid, succinic acid, tannic acid, tartaric acid, sulfuric acid, phosphoric acid, nitric acid, hydrochloric acid, sulfamic acid, carboxylic acid polymers, homo- or hetero-polymerized α hydroxy carboxylic acids including poly lactic acid and poly lactic-glycolic acid and mixtures of two or more said acids, said acidifying agent being present in the concentrate composition in an amount fixing the use from pH thereof below pH 5.

19. A soap concentrate composition as in claim 18 comprising a skin conditioner component selected from the group of conditioners and moisturing agents consisting of aloe vera, vitamins A, C, D, and E, menthol, thymol, tea tree oil, plant extract, sea weed extract, protein hydrolysates, fatty alcohols, fatty alcohol esters, sphingolipids, and mixtures of 2 or more said conditioners, in an amount ranging from 0.01 weight percent to about 20 weight percent based on the total weight percent of the concentrate composition.

20. A soap concentrate composition as in claim 18 comprising a generally regarded as safe GRAS compound component selected from the group of components consisting of benzoic acid, benzoic acid salts, benzoic acid esters, sorbic acid, sorbic acid salts, sorbic acid esters, parabens, alkyl lactylate esters, citrate esters, alkyl malate esters, alkyl glycolate esters, fatty acids, fatty acid salts and fatty acid esters, and mixtures of two or more said components.

21. A soap composition as in claim 1 that at pH<3 in diluted solution and/or dispersion form is cidal for *Mycobacterium tuberculosis* when applied to body surfaces or sanitizable surfaces within one-half to two minutes.

* * * * *

UNITED STATES PATENT AND TRADEMARK OFFICE
CERTIFICATE OF CORRECTION

PATENT NO    : 5,942,478
DATED        : August 24, 1999
INVENTOR(S)  : Lopes

It is certified that error appears in the above-identified patent and that said Letters Patent is hereby corrected as shown below:

Column 3, line 17, after "skin" and before "Lubricating" insert -- - --;

Column 3, line 29, delete "or" (second occurrence) and insert --to--;

Column 3, line 29, delete "and/to" and insert --and/or--.

Signed and Sealed this

Twenty-first Day of March, 2000

Attest:

Attesting Officer

Q. TODD DICKINSON

Commissioner of Patents and Trademarks